(12) United States Patent
Bol et al.

(10) Patent No.: US 9,709,494 B2
(45) Date of Patent: Jul. 18, 2017

(54) MEASURING ARRANGEMENT FOR MEASURING OPTICAL PROPERTIES OF A REFLECTIVE OPTICAL ELEMENT, IN PARTICULAR FOR MICROLITHOGRAPHY

(71) Applicant: Carl Zeiss SMT GmbH, Oberkochen (DE)

(72) Inventors: Johannes Bol, Oberkochen (DE); Hans-Juergen Rostalski, Oberkochen (DE)

(73) Assignee: Carl Zeiss SMT GmbH, Oberkochen (DE)

( * ) Notice: Subject to any disclaimer, the term of this patent is extended or adjusted under 35 U.S.C. 154(b) by 0 days.

(21) Appl. No.: 15/169,050

(22) Filed: May 31, 2016

(65) Prior Publication Data
US 2016/0274029 A1    Sep. 22, 2016

Related U.S. Application Data

(63) Continuation of application No. PCT/EP2014/075537, filed on Nov. 25, 2014.

(30) Foreign Application Priority Data

Nov. 28, 2013    (DE) .......................... 10 2013 224 435

(51) Int. Cl.
*G01J 1/42*        (2006.01)
*G01N 21/55*       (2014.01)
(Continued)

(52) U.S. Cl.
CPC ........... *G01N 21/55* (2013.01); *G01N 21/956* (2013.01); *G02B 17/0615* (2013.01);
(Continued)

(58) Field of Classification Search
CPC .. G01N 21/55; G02B 17/008; G02B 17/0631; G02B 17/0652; G02B 19/0047
See application file for complete search history.

(56) References Cited

U.S. PATENT DOCUMENTS

| 2,759,106 A | 8/1956 | Wolter |
| 6,856,395 B2 * | 2/2005 | Lebert .................... G01N 21/55 |
| | | 356/445 |

(Continued)

FOREIGN PATENT DOCUMENTS

| DE | 10138284 A1 | 2/2003 |
| DE | 102007051671 A1 | 5/2009 |

(Continued)

OTHER PUBLICATIONS

International Search Report in counterpart International Application No. PCT/EP2014/075537, mailed Mar. 27, 2015.
(Continued)

*Primary Examiner* — Kiho Kim
(74) *Attorney, Agent, or Firm* — Edell, Shapiro & Finnan, LLC (57) ABSTRACT

A measuring arrangement for measuring optical properties of a reflective optical element, in particular for microlithography, with an EUV light source (5), a detector (20) configured to detect EUV radiation reflected at the reflective optical element (10), and an imaging system (30, 40, 50, 60, 70, 80, 90), which images object points on the reflective optical element onto respective image points on the detector, wherein the imaging system is configured to reflect the EUV radiation, a first optical component (31, 41, 51, 61, 71, 81, 91), and at least one second optical component (32, 42, 52, 62, 72, 82, 92). Both at the first optical component and at the second optical component, reflection angles with respect to (Continued)

respective surface normals that respectively occur during reflection of the EUV radiation are at least 70°.

21 Claims, 8 Drawing Sheets

(51) Int. Cl.
    *G03F 7/20* (2006.01)
    *G01N 21/956* (2006.01)
    *G02B 19/00* (2006.01)
    *G02B 17/06* (2006.01)

(52) U.S. Cl.
    CPC ..... *G02B 19/0023* (2013.01); *G02B 19/0085* (2013.01); *G02B 19/0095* (2013.01); *G03F 7/7055* (2013.01); *G03F 7/70316* (2013.01); *G03F 7/70591* (2013.01); *G03F 7/70958* (2013.01); *G01N 2021/557* (2013.01); *G01N 2021/95676* (2013.01)

(56) References Cited

U.S. PATENT DOCUMENTS

| | | | |
|---|---|---|---|
| 6,864,490 B1* | 3/2005 | Underwood | G01J 3/18 250/461.1 |
| 7,016,030 B2 | 3/2006 | Naulleau | |
| 2002/0175690 A1 | 11/2002 | Lebert et al. | |
| 2003/0095623 A1 | 5/2003 | Singer et al. | |
| 2005/0195506 A1* | 9/2005 | McGuire | G02B 17/008 359/861 |
| 2007/0296973 A1* | 12/2007 | Kiers | G01N 21/21 356/369 |
| 2011/0001947 A1 | 1/2011 | Dinger et al. | |
| 2013/0141707 A1* | 6/2013 | Baer | B82Y 10/00 355/67 |
| 2014/0132941 A1 | 5/2014 | Mann et al. | |

FOREIGN PATENT DOCUMENTS

| | | |
|---|---|---|
| DE | 102008009600 A1 | 8/2009 |
| EP | 1249698 A1 | 10/2002 |
| WO | 2006050891 A1 | 5/2006 |
| WO | 2007054291 A1 | 5/2007 |
| WO | 2008092707 A1 | 8/2008 |

OTHER PUBLICATIONS

Zeitner, U. D. et al., "Schwarzschild-Objective-Based EUV Micro Exposure Tool", SPIE—Proceedings, vol. 6151, Mar. 2006.
Office Action in corresponding German Application No. 102013224435.5, dated Nov. 21, 2014.
International Search Report and Written Opinion in counterpart International Application No. PCT/EP2014/075537, dated May 31, 2016, along with an English language translation.

* cited by examiner

MEASURING ARRANGEMENT FOR MEASURING OPTICAL PROPERTIES OF A REFLECTIVE OPTICAL ELEMENT, IN PARTICULAR FOR MICROLITHOGRAPHY

CROSS REFERENCE TO RELATED APPLICATIONS

This is a Continuation of International Application PCT/EP2014/075537, which has an international filing date of Nov. 25, 2014, and the disclosure of which is incorporated in its entirety into the present Continuation by reference. The following disclosure is also based on and claims the benefit of and priority under 35 U.S.C. §119(a) to German Patent Application No. DE 10 2013 224 435.5, filed Nov. 28, 2013, which is also incorporated in its entirety into the present Continuation by reference.

FIELD OF THE INVENTION

The invention relates to a measuring arrangement for measuring optical properties of a reflective optical element, in particular for microlithography.

BACKGROUND

Microlithography is used for producing microstructured components, such as for example integrated circuits or LCDs. The microlithography process is carried out in a so-called projection exposure apparatus having an illumination device and a projection lens. The image of a mask (reticle) illuminated by the illumination device is in this case projected by the projection lens onto a substrate (for example a silicon wafer) coated with a light-sensitive layer (photoresist) and arranged in the image plane of the projection lens, in order to transfer the mask structure to the light-sensitive coating of the substrate.

In projection lenses designed for the EUV range, i.e. at wavelengths of e.g. approximately 13 nm or approximately 7 nm, owing to the lack of availability of suitable light-transmissive refractive materials, mirrors are used as optical components for the imaging process. Such EUV mirrors typically have a mirror substrate and a reflection layer stack—constructed from a multiplicity of layer packets—for reflecting the electromagnetic radiation incident on the optically effective surface. In the illumination device of a microlithographic projection exposure apparatus designed for operation in the EUV range, in particular the use of facet mirrors in the form of field facet mirrors and pupil facet mirrors as focusing components is known for example from DE 10 2008 009 600 A1. Such facet mirrors are constructed from a multiplicity of individual mirrors or mirror facets.

In practice there is often a need to measure the reflection properties of such mirrors or mirror arrangements with the highest possible accuracy and also—in particular in the case of mirror arrangements comprising comparatively small mirrors such as the aforementioned facet mirrors—to measure these properties with high spatial resolution. However, here the problem arises that an ever-increasing reduction in the respective measuring spots that is conceivable for this purpose has limits, to the extent that the reduction in the measuring spots is accompanied by an increase in the beam divergence or reduction in the intensity, which in turn has the effect that a relatively wide spectrum of different angles of incidence is achieved, which ultimately impairs the spectral resolution achieved in the measurement.

It is also known for the spatially resolved measurement of the reflection properties of a reflective optical element to arrange a detector, for example in the form of a CCD camera, in the far field of the reflective surface to be examined, which is illuminated over its full surface area. However, here the further problem arises that roughnesses of the reflective surface to be examined (unless for example it is well polished or the reflection coating is uniformly thick) lead to deformations of the wave fronts that are respectively reflected at this surface, which results in undesired interference effects at the detector. Since it is not easy to distinguish at the detector whether the measured variation in the intensity distribution is attributable to inhomogeneities in the reflectivity or unevennesses in the reflective surface examined, the interference effects mentioned lead to an impairment of the measuring accuracy.

As prior art, reference is made only by way of example to U.S. Pat. No. 2,759,106, U.S. Pat. No. 7,016,030 B2 and the publication U. D. Zeitner et al.: "Schwarzschild-Objective-Based EUV Micro Exposure Tool", SPIE-Proceedings volume 6151, March 2006.

SUMMARY

An object of the present invention is to provide a measuring arrangement for measuring optical properties of a reflective optical element, in particular for microlithography, that makes a high spatial resolution possible, while avoiding at least to a great extent the problems described above.

A measuring arrangement according to one aspect of the invention for measuring optical properties of a reflective optical element, in particular for microlithography, has:
- an EUV light source;
- a detector configured to detect EUV radiation reflected at the reflective optical element; and
- an imaging system, which images object points on the reflective optical element onto respective image points on the detector;
- wherein the imaging system is configured to reflect the EUV radiation, and has a first optical component and at least one second optical component; and
- wherein, both at the first optical component and at the second optical component, the reflection angles in relation to the respective surface normals that respectively occur during the reflection of the EUV radiation are at least 70° (corresponding to a "grazing incidence").

This aspect of the invention is based in particular on the concept of using an imaging system between the reflective surface to be examined of the reflective optical element ("sample") and the detector for imaging locations or object points on the sample individually onto locations or image points on the detector, with the consequence that on each of the image points concerned on the detector there is only ever generated the intensity that comes from a location or object point of the reflective surface of the reflective optical element or sample to be examined.

In other words, each point on the detector (for example a CCD camera) corresponds exactly to a point on the sample and no longer to a "mixture" of multiple points on the sample (illuminating a common point on the camera). Since it is always the case that only one (object) point of the reflective optical element or the sample to be examined is imaged onto one point of the detector, there is consequently no longer any superposing of multiple intensities from multiple (object) points of the sample on one (image) point on the detector, so that the undesired interference patterns described at the beginning are avoided.

As a result, comparatively high spatial resolutions (for example below 100 µm, in particular below 20 µm) can be achieved.

Since, furthermore, the optical components that are present in the imaging system used in the measuring arrangement according to the invention between the reflective optical element to be examined and the detector are respectively operated with grazing incidence, a narrowband wavelength limitation—that exists for instance in the case of an arrangement with perpendicular incidence—is also avoided, creating the possibility of realizing broadband reflectometry. In particular, a reflection spectrum of (object) points on the sample to be examined can be determined, so that more comprehensive information with regard to the reflection properties (for example including the level and spectral position of the maximum reflectivity and the level and spectral position of the adjacent reflection minima, if present, in a wavelength range) can be obtained, and corresponding conclusions can be drawn concerning sample properties, such as for example reflection layer thicknesses.

A further advantage that is achieved according to the invention is that, for instance in the application in microscopy, the broadband capability provided by the measuring arrangement according to the invention also makes it possible to achieve a sufficiently spatially resolved or high-contrast examination of structures which have individual substructures reflecting at wavelengths that are different from one another. In such a case—as explained in more detail hereinbelow—instead of a microscopic examination of the overall structure at a single wavelength, a microscopic examination may be performed in multiple substeps, with a differently set wavelength or light source in each case, or else using a sufficiently broadband light source, so that, instead of a uniform reflection (achieved for example when using a single, mid-range wavelength), the individual structures can be resolved with comparatively high contrast in accordance with the wavelength that is used.

According to one embodiment, the first optical component and the second optical component respectively have a conic cross section.

According to one embodiment, the first optical component is an ellipsoid mirror. The second optical component may be for example a hyperboloid mirror or likewise an ellipsoid mirror. It may be the case here in particular that a focal point of the first optical component and a focal point of the second optical component coincide.

According to one embodiment, the detector has a CCD camera or a CMOS sensor.

According to one embodiment, the reflective optical element is a mirror or a microlithographic projection exposure apparatus.

According to one embodiment, the reflective optical element is a mirror facet of a facet mirror, in particular a field facet mirror or a pupil facet mirror, of an illuminating device of a microlithographic projection exposure apparatus.

According to one embodiment, the reflective optical element is a microlithography mask. The invention can consequently also be advantageously realized in particular in a mask inspection system for the inspection of microlithography masks.

According to one embodiment, the EUV light source is a light source for generating EUV radiation with different wavelengths over a wavelength interval of at least $\Delta\lambda=1$ nm, in particular of at least $\Delta\lambda=3$ nm, more particularly of at least $\Delta\lambda=5$ nm, more particularly of at least $\Delta\lambda=10$ nm, and more particularly of at least $\Delta\lambda=20$ nm. The EUV light may be designed as a broadband light source for generating EUV radiation in a continuous wavelength spectrum or as a light source that can be set to different narrowband wavelength ranges.

According to one embodiment, the measuring arrangement has over a predetermined wavelength interval a lateral spatial resolution (sometimes also referred to as the line width or CD="critical dimension") of less than 100 µm, in particular of less than 50 µm, more particularly of less than 20 µm, and more particularly of less than 10 µm.

According to one embodiment, this wavelength interval is at least $\Delta\lambda=3$ nm, more particularly at least $\Delta\lambda=5$ nm, more particularly at least $\Delta\lambda=10$ nm, and more particularly at least $\Delta\lambda=20$ nm.

According to a further aspect, the invention also relates to a measuring arrangement for measuring optical properties of a reflective optical element, in particular for microlithography, with
 an EUV light source;
 a detector configured to detect EUV radiation reflected at the reflective optical element; and
 an imaging system, which images object points on the reflective optical element onto respective image points on the detector;
 wherein the measuring arrangement has over a predetermined wavelength interval of at least $\Delta\lambda=3$ nm a lateral spatial resolution of less than 100 µm.

The invention also relates furthermore to a mask inspection system that has a measuring arrangement with the features described above.

The invention also relates furthermore to an EUV microscope that has a measuring arrangement with the features described above.

According to a further aspect, the invention also relates to a method for measuring optical properties of a reflective optical element, in particular for microlithography, wherein the reflective optical element is illuminated with EUV radiation of an EUV light source and wherein object points on the reflective optical element are imaged with an imaging system onto respective image points on a detector, utilizing a measuring arrangement with the features described above.

According to one embodiment, the imaging of the object points on the reflective optical element onto respective image points on a detector is performed in a plurality of substeps, which differ from one another with regard to the operating wavelength utilized in this imaging. As a result, as already described above, instead of a uniform reflection (achieved for example when using a single, mid-range wavelength), this allows the individual structures to be resolved with comparatively high contrast in accordance with the wavelength that is used.

Further configurations of the invention can be gathered from the description and the dependent claims.

The invention is explained in greater detail below on the basis of exemplary embodiments illustrated in the accompanying figures.

BRIEF DESCRIPTION OF THE DRAWINGS

In the figures.

DETAILED DESCRIPTION

Figure 1:
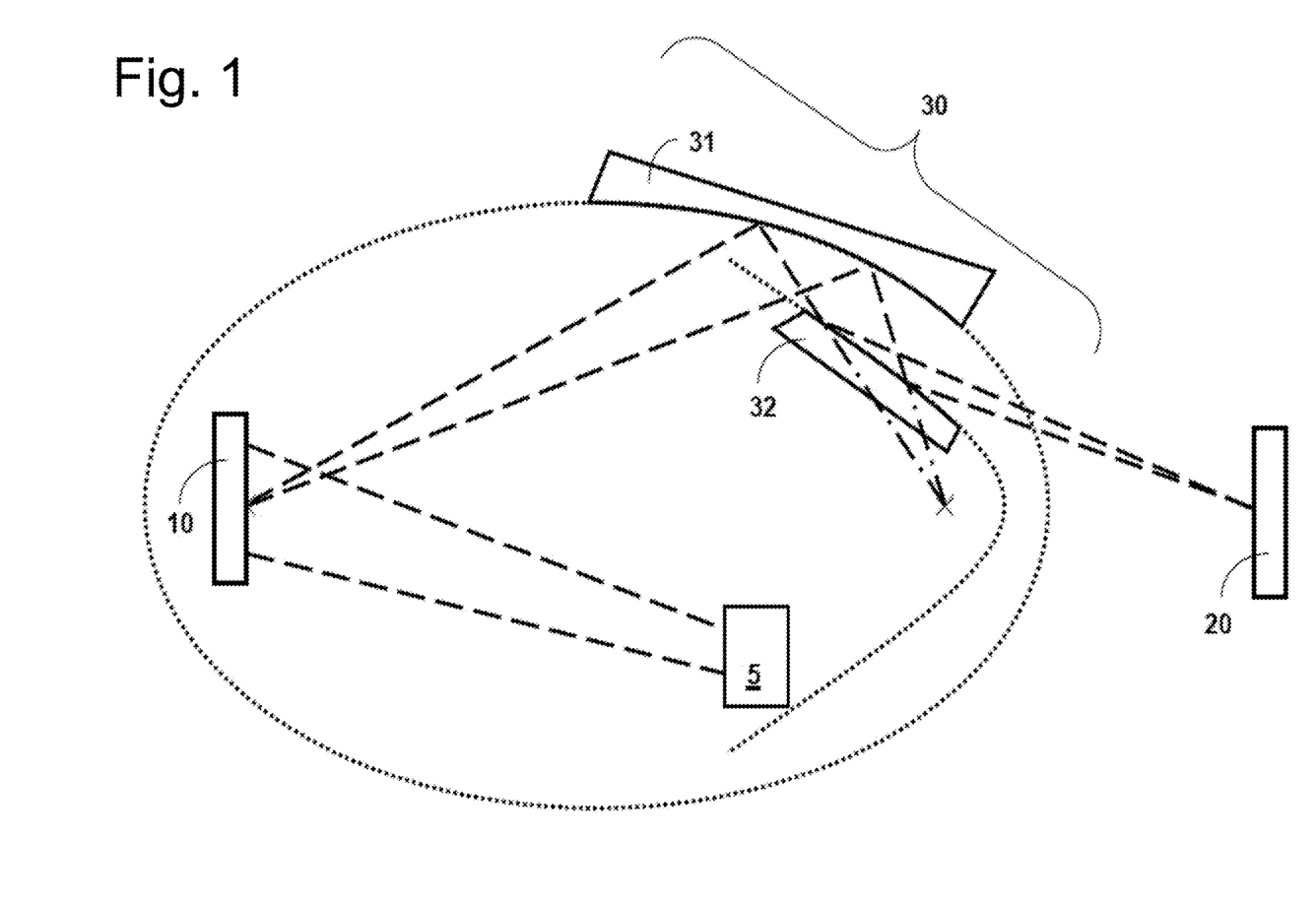
FIG. 1 shows a schematic representation of a measuring arrangement according to the invention.

There follows firstly a description of the basic construction of a measuring arrangement according to the invention for measuring the reflection properties of a reflective optical element for microlithography on the basis of an exemplary embodiment with reference to the schematic illustration of FIG. 1.

In this measuring arrangement, according to FIG. 1, a detector 20 in the form of a CCD camera is arranged in the projected image of a reflective optical element 10 irradiated by an EUV light source 5 with electromagnetic EUV radiation. The imaging of the EUV radiation emitted by the EUV light source 5 and reflected by the reflective optical element 10 onto the CCD camera is performed by an imaging system 30, which in the exemplary embodiment of FIG. 1 has a first optical component 31 in the form of an ellipsoid mirror and a second optical component 32 in the form of a hyperboloid mirror (the progression of the corresponding ellipse or hyperbola being represented in FIG. 1 by respective dotted lines). The reflective optical element 10 may in this case be located either in the far field or at a focal point of the EUV light source 5.

This involves a "grazing incidence" respectively taking place at the optical components 31 and 32 of the imaging system 30, to the extent that the reflection angle of the electromagnetic EUV radiation in relation to the perpendicular to the respective optical component 31 or 32 is at least 70°.

In further embodiments, a CMOS sensor may also be used as the detector 20. Furthermore, a (CMOS or CCD) sensor that is used as the detector 20 may also be configured with rear exposure. Furthermore, the corresponding image sensor may also be provided with a fluorescent layer (for example for the transformation of electromagnetic EUV radiation into visible light for the purpose of simplified detection).

FIGS. 2A-2F show schematic representations for explaining further different embodiments of an imaging system that can be used in the measuring arrangement according to the invention. The representations of 2A-2F merely serve here for illustrating different possibilities for combining optical elements in the imaging system concerned, it also being possible in each case by suitable choice of the parameters of these optical components (i.e. of the respective ellipsoid mirror or hyperboloid mirror) to ensure the aforementioned grazing incidence on the mirror surfaces concerned in a way analogous to FIG. 1.

Figure 2A:
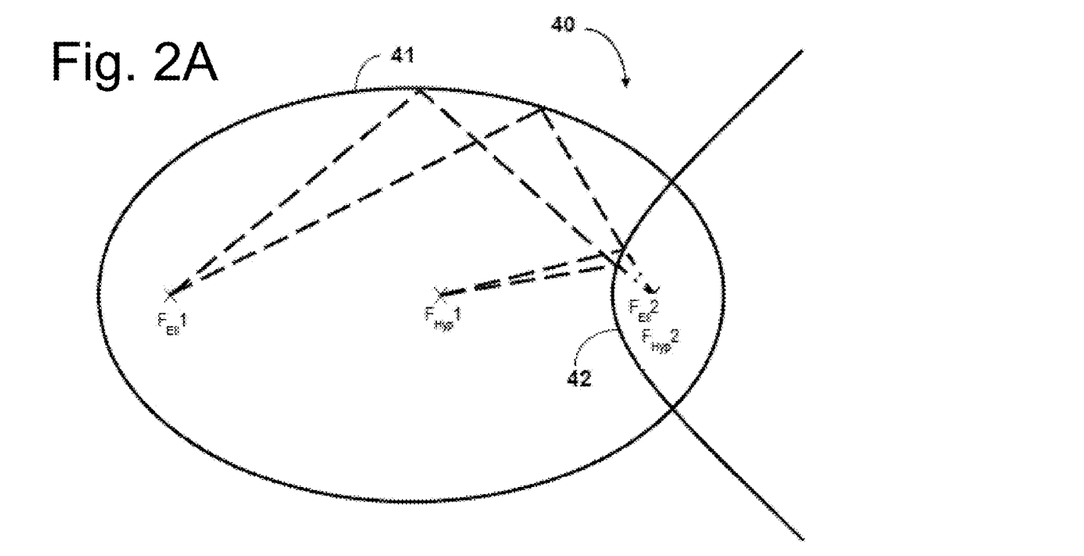
FIGS. 2A-2F show schematic representations for explaining different embodiments of an imaging system that can be used in the measuring arrangement according to the invention.

According to FIG. 2A, an imaging system 40 that is used in the measuring arrangement according to the invention has a first optical component 41 in the form of an ellipsoid mirror and a second optical component 42 in the form of a hyperboloid mirror, wherein the second focal point of the ellipsoid and the second focal point of the hyperboloid coincide and wherein the convex side of the hyperbola is used.

Figure 2B:
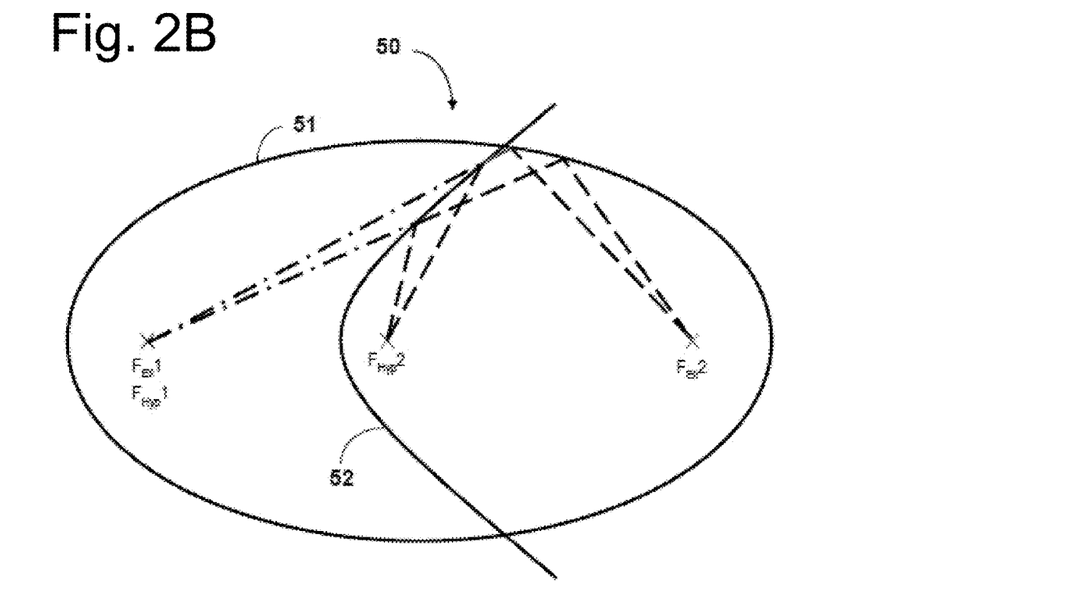

According to FIG. 2B, in a further embodiment an imaging system 50 that is used in the measuring arrangement according to the invention has a first optical component 51 in the form of an ellipsoid mirror and a second optical component 52 in the form of a hyperboloid mirror, wherein the first focal point of the hyperboloid and the first focal point of the ellipsoid coincide and wherein the concave side of the hyperboloid is used (this system may also be referred to as a "Wolter Type I system").

Figure 2C:
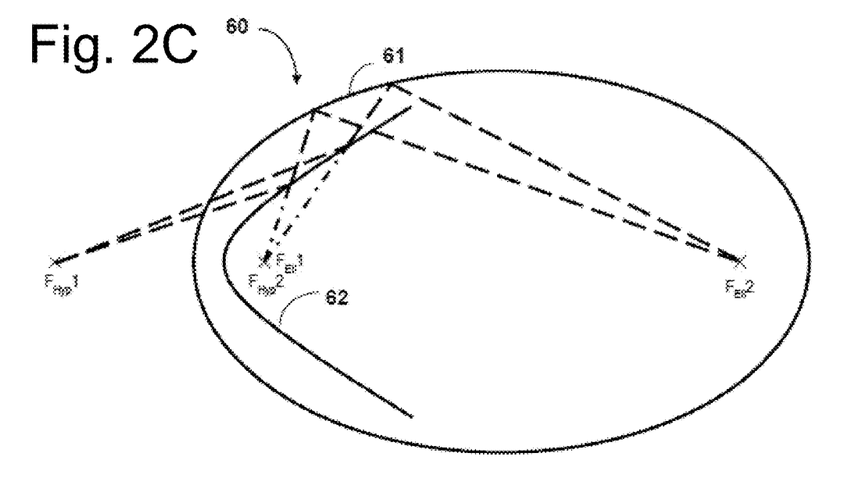

According to FIG. 2C, in a further embodiment an imaging system 60 that is used in the measuring arrangement according to the invention has a first optical component 61 in the form of an ellipsoid mirror and a second optical component 62 in the form of a hyperboloid mirror, wherein the second focal point of the hyperboloid and the first focal point of the ellipsoid coincide (this system may also be referred to as a "Wolter Type II system").

Figure 2D:
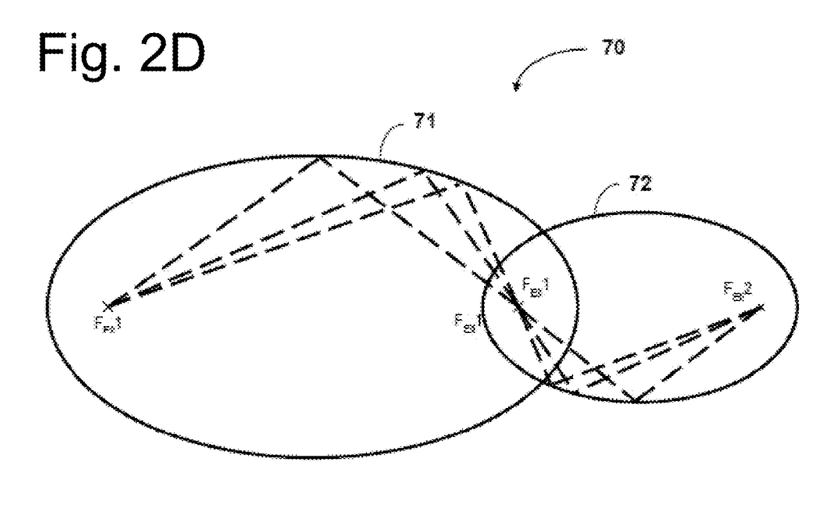

According to FIG. 2D, an imaging system 70 that is used in a further embodiment in the measuring arrangement according to the invention has a first optical component 71 in the form of an ellipsoid mirror and a second optical component 72 in the form of a ellipsoid mirror, wherein the second focal point of the first ellipsoid and the first focal point of the second ellipsoid coincide.

Figure 2E:
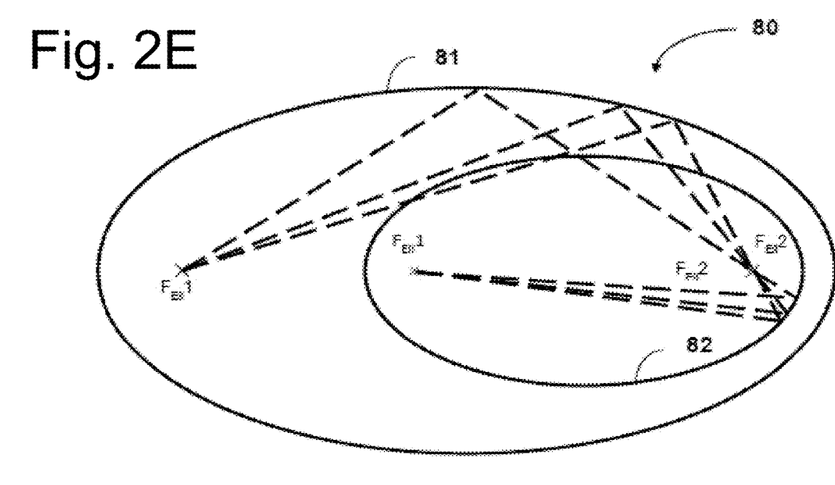

According to FIG. 2E, in a further embodiment an imaging system 80 that is used in the measuring arrangement according to the invention has a first optical component 81 in the form of an ellipsoid mirror and a second optical component 82 in the form of an ellipsoid mirror, wherein the second focal point of the first ellipsoid and the second focal point of the second ellipsoid coincide.

Figure 2F:
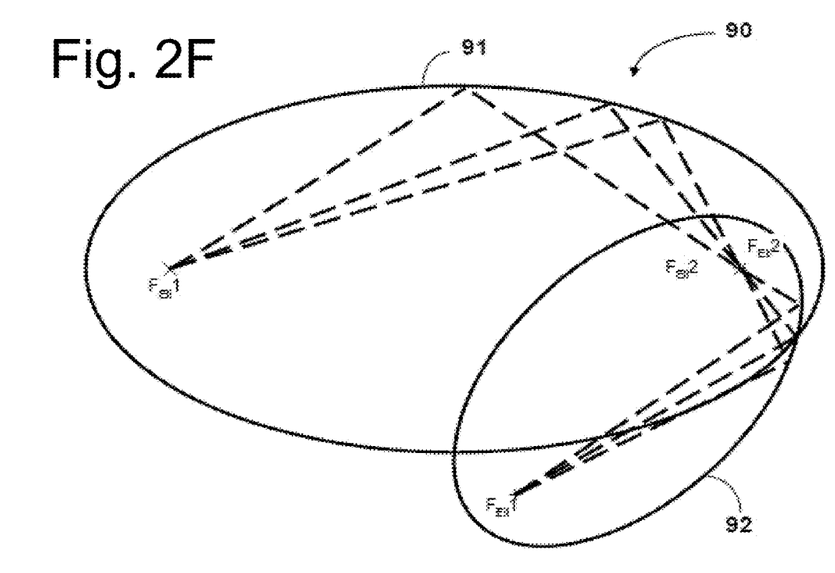

Even though in the embodiments described above the axes of rotation of the optical components concerned of the imaging system coincide in each case, the invention is not restricted to this. For the purpose of illustration, FIG. 2F shows merely by way of example an arrangement which is modified in comparison with FIG. 2E and in which in an imaging system 90 the second optical component 92 in the form of the ellipsoid mirror has been turned with the axis of rotation of the ellipsoid with respect to the first optical component 91.

Furthermore, the combinations of optical components that are represented in FIGS. 2A-2F may be realized for both directions of light propagation (opposite one another) in the imaging system concerned. Furthermore, the optical components in the imaging system concerned are not necessarily rotationally symmetrical. The combinations represented may also be respectively realized with plane-elliptical or plane-hyperboloidal mirrors.

Figure 3:
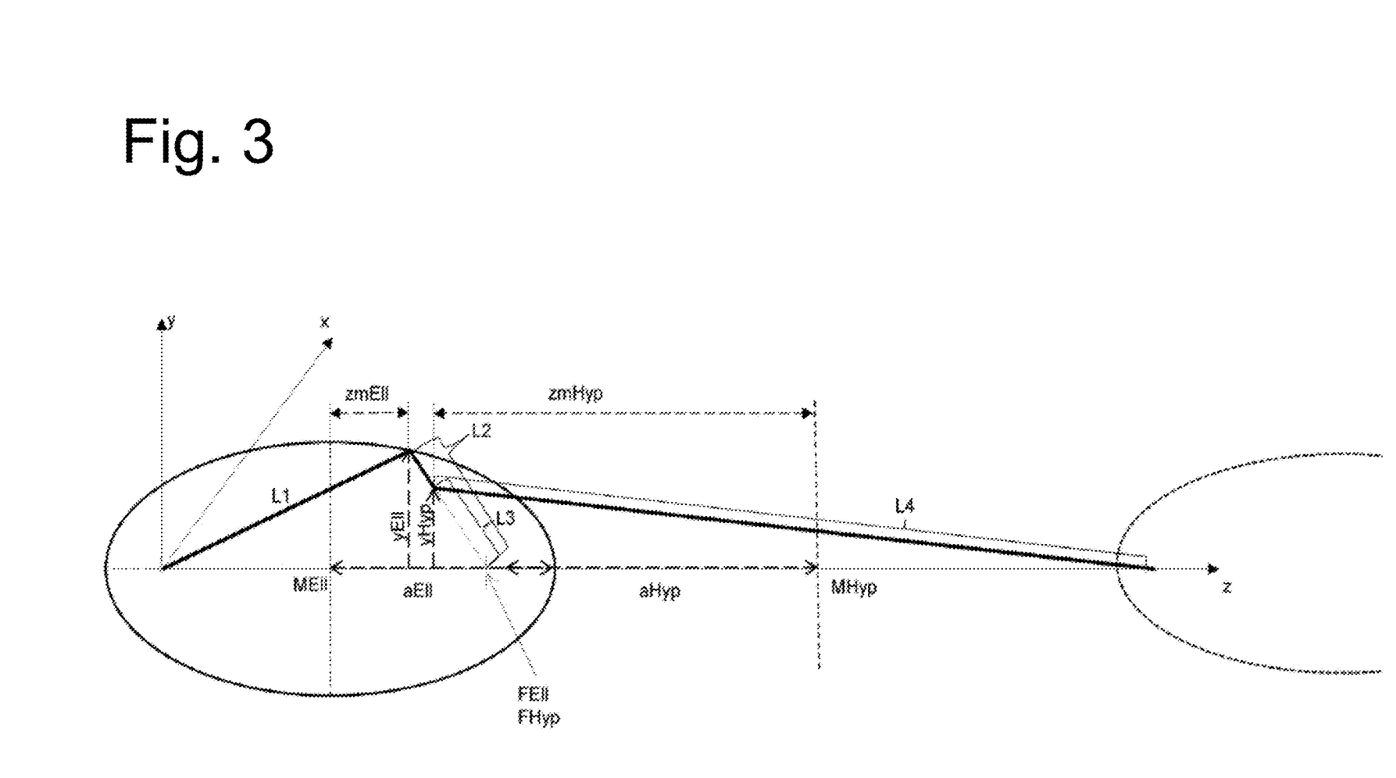
FIG. 3 shows a schematic representation for explaining a specific exemplary embodiment of the present invention.

In Table 1 and Table 2, the design data of an imaging system that can be used in the measuring arrangement according to the invention, which has the basic construction described respectively on the basis of FIG. 1 and FIG. 2A, are given merely by way of example and to indicate a specific exemplary embodiment. FIG. 3 serves for illustrating and defining the mirror parameters that are contained in Tables 1 and 2.

A particularly advantageous aspect of this design is that the two optical components or mirrors of the imaging system are relatively close together, it being possible for these mirrors to be adjusted in a suitable way in relation to one another to the required adjusting accuracy (which may for example be of the order of magnitude of 1 µm) outside the actual measuring arrangement and then installed together in the measuring arrangement.

Figure 4:
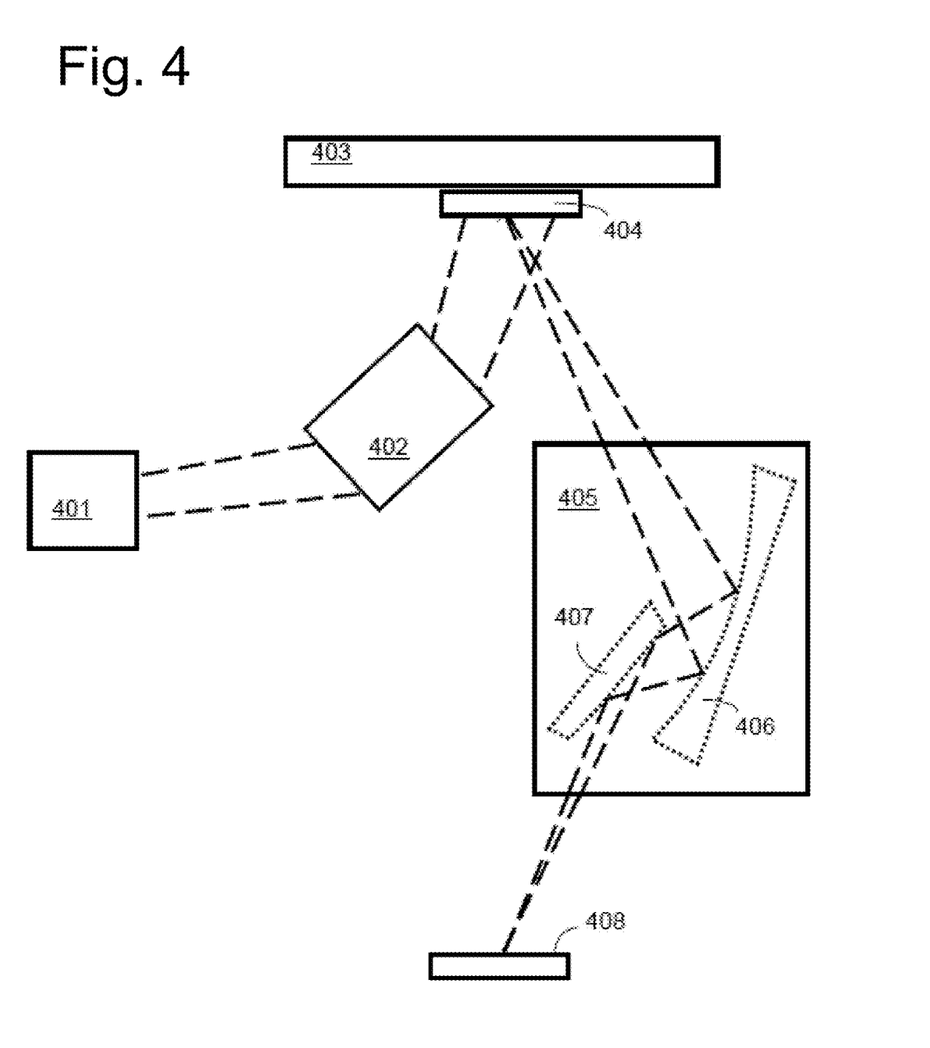
FIG. 4 shows a schematic representation for explaining a possible application of the present invention in a mask inspection system.

FIG. 4 shows in a merely schematic representation the possible construction of a mask inspection system for the inspection of microlithography masks by using a measuring arrangement according to the invention.

According to FIG. 4, electromagnetic radiation (for example at a wavelength in the EUV range) of a light source 401 is incident on an illumination optical unit 402 for illuminating a microlithography mask 404 located on a mask stage 403. The light source 401 may for example have an adjustable wavelength (for example 6.7 nm or 13.5 nm). In further embodiments, the light source 401 may also be configured as a broadband light source (which for example generates both electromagnetic radiation at a wavelength of 6.7 nm and electromagnetic radiation at a wavelength of 13.5 nm). Furthermore, the illumination optical unit 402 may have an adjustable wavelength selection.

According to FIG. 4, the electromagnetic radiation reflected at the microlithography mask 404 is incident on an imaging system 405, which may be configured according to the embodiments described above and in particular has optical components 406 and 407 configured according to the aforementioned embodiments. By analogy with the embodiments described above, the electromagnetic radiation emerging from the imaging system 405 is incident on a detector 408 (for example a CCD camera or a CMOS sensor).

Figure 5:
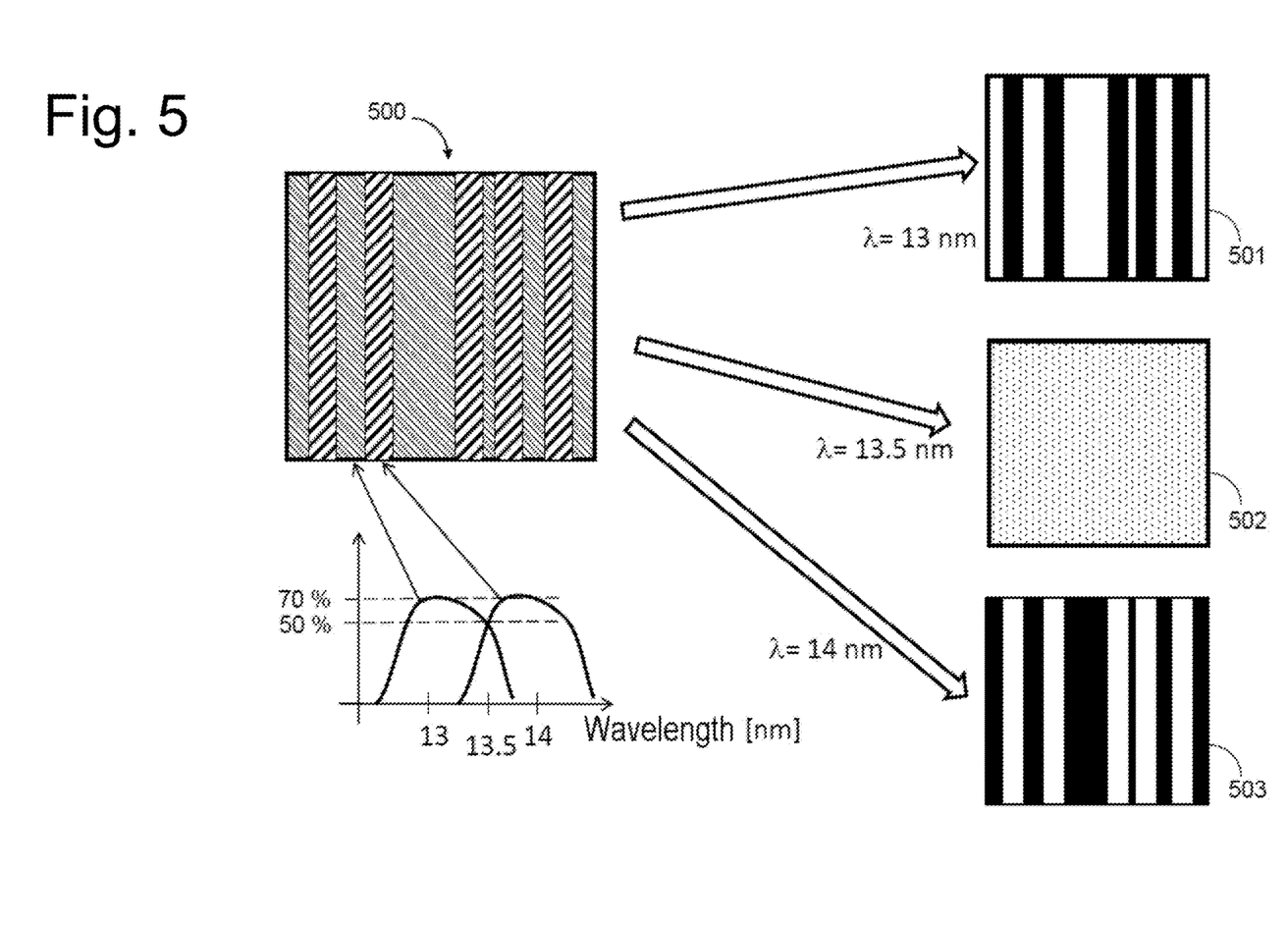
FIG. 5 shows a schematic representation for explaining a further application of the invention in an EUV microscope.

FIG. 5 shows a schematic representation for explaining a further advantageous application of the invention in a microscope, in particular an EUV microscope with variable wavelength. In FIG. 5, "500" represents a sample which is to be microscopically examined and, in the simple exemplary embodiment represented, has a stripe pattern comprising stripes 501a, 501b, . . . of a first layer thickness and stripes 502a, 502b, . . . of a second layer thickness that is different from the first layer thickness, the reflectance that is schematically plotted in the diagram of FIG. 5 having its maximum of 70% for these stripes at wavelengths that are different from one another (about 13 nm and about 14 nm). As merely schematically represented in FIG. 5, a microscopic examination using a single wavelength of 13.5 mm would only produce a low-contrast projected image 502, with substantially uniform intensity, whereas the microscopic examination both at a first wavelength of 13 nm and at a second wavelength of 14 nm for both patterns of stripes 501a, 501b, . . . and 502a, 502b, . . . respectively produces projected images 501 and 503 with high-contrast resolution. The broadband capability that can be achieved with the measuring arrangement according to the invention can in other words be used to microscopically examine with increased contrast or high spatial resolution different structures that reflect electromagnetic radiation at wavelengths that are different from one another.

Figure 6:
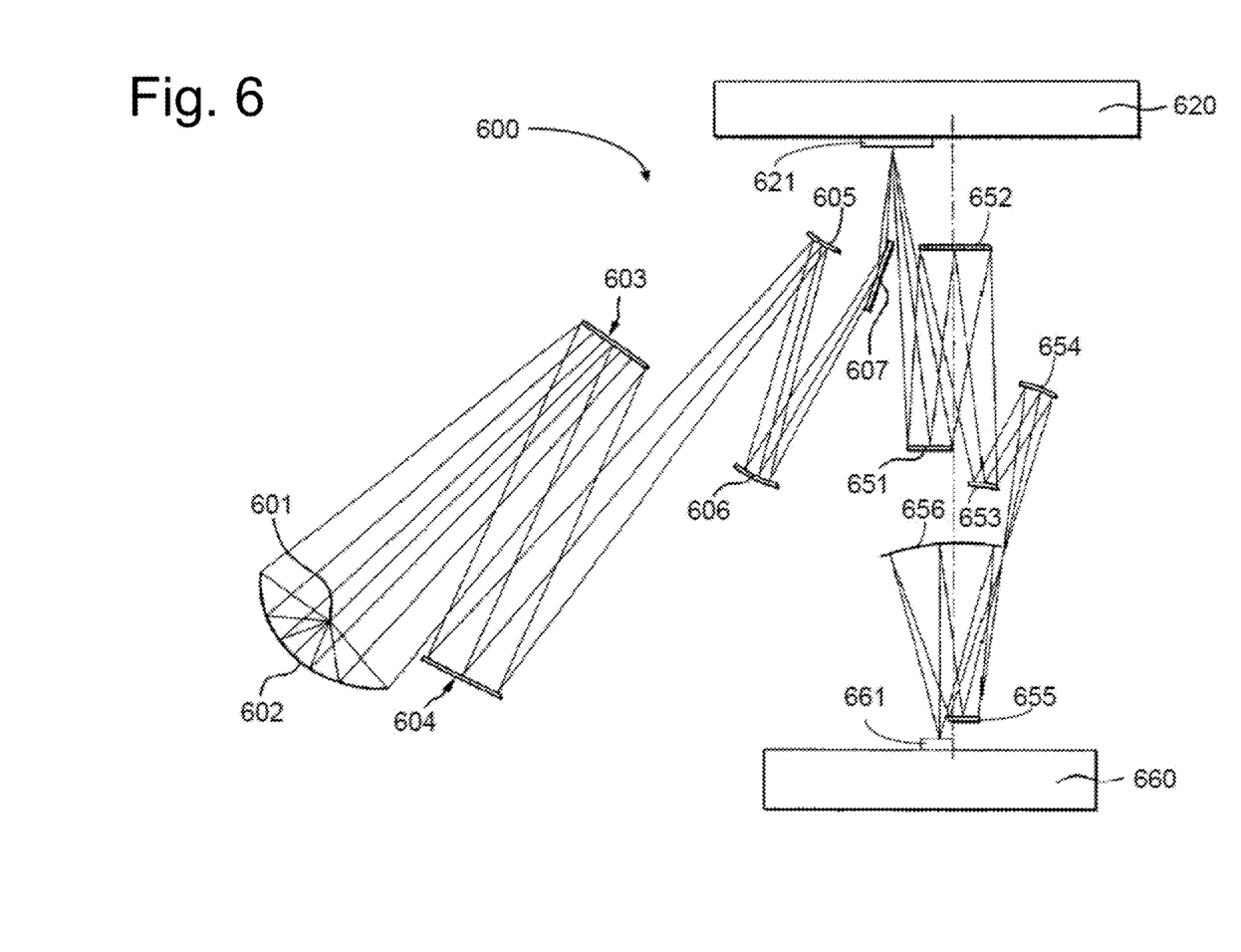
FIG. 6 shows a schematic representation of the possible construction of a microlithographic projection exposure apparatus.

In further applications, the measuring arrangement according to the invention may also be used for determining the reflection properties of a mirror of a microlithographic projection exposure apparatus, which may be designed in particular for operation in the EUV range. FIG. 6 shows in this respect a merely schematic representation of a projection exposure apparatus that is given by way of example and is designed for operation in the EUV range.

According to FIG. 6, an illumination device in a projection exposure apparatus 600 designed for EUV comprises a field facet mirror 603 and a pupil facet mirror 604. The light from a light source unit comprising a plasma light source 601 and a collector mirror 602 is directed onto the field facet mirror 603. A first telescope mirror 605 and a second telescope mirror 606 are arranged in the light path downstream of the pupil facet mirror 604. Arranged downstream in the light path is a deflection mirror 607, which directs the radiation incident on it onto an object field in the object plane of a projection lens comprising six mirrors 651-656. Arranged on a mask stage 620 at the location of the object field is a reflective structure-bearing mask 621, which with the aid of the projection lens is imaged into an image plane, in which there is a substrate 661 coated with a light-sensitive layer (photoresist) on a wafer stage 660.

Even though the invention has been described on the basis of specific embodiments, numerous variations and alternative embodiments are evident to the person skilled in the art, e.g. through combination and/or exchange of features of individual embodiments. Accordingly, such variations and alternative embodiments are concomitantly encompassed by the present invention, and the scope of the invention is restricted only within the meaning of the appended patent claims and equivalents thereof.

TABLE 1

Design data of ellipsoid

| Description | Desig. | Value | Units |
|---|---|---|---|
| Radius at the vertex | r | −39.317038 | mm |
| Conic constant | k | −0.952999221 | |
| Numerical eccentricity | eps | 0.97621679 | |
| Semi-axis in the z direction | aEll | −836.5188585 | mm |
| Semi-axis in the y direction | b | 181.3544699 | mm |
| Linear eccentricity | e | −816.6237548 | mm |
| Positional indication with respect to surface vertex | | | |
| Midpoint in the z direction (=a) | z | −836.5188585 | mm |
| Target point in the y direction | yEll | 151.779 | mm |
| Target point in the z direction | zEll | −378.67 | mm |
| Extent: | | | |
| From | z1 | −353 | mm |
| To | z2 | −404 | mm |
| From (in relation to the target point) | z1r | −25.67 | mm |
| To (in relation to the target point) | z2r | 25.33 | mm |
| Width | 2x | 13.2 | mm |
| Positional indications with respect to midpoint (MEll) | | | |
| Target point in the z direction | zmEll | 457.8488585 | mm |
| Indications with respect to the triangle comprising target point and focal points | | | |
| Leg 1 | L1 | 1291.37751 | mm |
| Leg 2 | L2 | 381.6602071 | mm |
| Half deflecting angle at the target point | Theta | 14.81934 | ° |

TABLE 2

Design data of hyperboloid

| Description | Desig. | Value | Units |
|---|---|---|---|
| Radius at the vertex | r | −15.055952 | mm |
| Conic constant | k | −1.004191885 | |
| Numerical eccentricity | eps | 1.002093751 | |
| Semi-axis in the z direction | aHyp | 3591.690135 | mm |
| Semi-axis in the y direction | b | 232.543145 | mm |
| Linear eccentricity | e | 3599.210238 | mm |
| Positional indication with respect to surface vertex | | | |
| Midpoint in the z direction (=a) | z | 3591.690135 | mm |
| Target point in the y direction | yHyp | 75.939 | mm |
| Target point in the z direction | zHyp | −186.662 | mm |
| Extent: | | | |
| From | z1 | −169 | mm |
| To | z2 | −204 | mm |
| From (in relation to the target point) | z1r | −17.662 | mm |
| To (in relation to the target point) | z2r | 17.338 | mm |
| Width | 2x | 7 | mm |

TABLE 2-continued

Design data of hyperboloid

| Description | Desig. | Value | Units |
|---|---|---|---|
| Positional indications with respect to midpoint (MHyp) | | | |
| Target point in the z direction | zmHyp | −3778.352135 | mm |
| Indications with respect to the triangle comprising target point and focal points | | | |
| Leg 1 | L3 | −186.6727871 | mm |
| Leg 2 | L4 | 6461.31911 | mm |
| Half deflecting angle at the target point | Theta | 11.10787 | ° |

What is claimed is:

1. A measuring arrangement for measuring optical properties of a reflective optical element, comprising:
   an extreme ultraviolet (EUV) light source;
   a detector configured to detect EUV radiation reflected from the reflective optical element; and
   an imaging system, arranged downstream from the reflective optical element and upstream from the detector and which images the radiation reflected from object points on the reflective optical element onto respective image points on the detector;
   wherein the imaging system is configured to reflect the EUV radiation and comprises a first optical component and at least one second optical component; and
   wherein, both at the first optical component and at the second optical component, reflection angles with respect to respective surface normals that respectively occur during reflection of the EUV radiation are at least 70°.

2. The measuring arrangement as claimed in claim 1, wherein the first optical component and the second optical component have surfaces forming respective conic cross sections.

3. The measuring arrangement as claimed in claim 1 wherein the first optical component comprises an ellipsoid mirror.

4. The measuring arrangement as claimed in claim 1, wherein the second optical component comprises a hyperboloid mirror.

5. The measuring arrangement as claimed in claim 1, the second optical component is an ellipsoid mirror.

6. The measuring arrangement as claimed in claim 1, wherein the detector comprises a CCD camera or a CMOS sensor.

7. The measuring arrangement as claimed in claim 1, configured to measure the optical properties of at least one of the following reflective optical elements:
   a mirror of a microlithographic projection exposure apparatus;
   a mirror facet of a facet mirror of an illumination device of a microlithographic projection exposure apparatus; and
   a microlithography mask.

8. The measuring arrangement as claimed in claim 1, wherein the EUV light source is a broadband or an adjustable light source configured to generate EUV radiation with different wavelengths over a wavelength interval of at least $\Delta\lambda=1$ nm.

9. The measuring arrangement as claimed in claim 8, wherein the EUV light source is configured to generate EUV radiation with different wavelengths over a wavelength interval of at least $\Delta\lambda=20$ nm.

10. The measuring arrangement as claimed in claim 1, having, over a predetermined wavelength interval, a lateral spatial resolution of less than 100 µm.

11. The measuring arrangement as claimed in claim 10, having, over the predetermined wavelength interval, a lateral spatial resolution of less than 10 µm.

12. The measuring arrangement as claimed in claim 10, wherein the predetermined wavelength interval is at least $\Delta\lambda=3$ nm.

13. The measuring arrangement as claimed in claim 10, wherein the predetermined wavelength interval is at least $\Delta\lambda=20$ nm.

14. A mask inspection system comprising a measuring arrangement as claimed in claim 1.

15. An EUV microscope comprising a measuring arrangement as claimed in claim 1.

16. A method for measuring optical properties of a reflective optical element with a measuring arrangement as claimed in claim 1, comprising:
   illuminating the reflective optical element with EUV radiation of the EUV light source, and
   imaging object points on the reflective optical element with an imaging system onto respective image points on the detector.

17. The method as claimed in claim 16, wherein the imaging of the object points on the reflective optical element onto the respective image points on the detector is performed in a plurality of substeps, which differ from one another with regard to the operating wavelength utilized in the imaging.

18. A measuring arrangement for measuring optical properties of a reflective optical element, comprising:
   an extreme ultraviolet (EUV) light source;
   a detector configured to detect EUV radiation reflected at the reflective optical element; and
   an imaging system, which images object points on the reflective optical element onto respective image points on the detector;
   wherein the imaging system is configured to reflect the EUV radiation and comprises a first optical component and at least one second optical component; and
   wherein, both at the first optical component and at the second optical component, reflection angles with respect to respective surface normals that respectively occur during reflection of the EUV radiation are at least 70°,
   wherein a focal point of the first optical component and a focal point of the second optical component coincide.

19. A measuring arrangement for measuring optical properties of a reflective optical element, comprising:
   an extreme ultraviolet (EUV) light source;
   a detector configured to detect EUV radiation reflected from the reflective optical element; and
   an imaging system arranged downstream from the reflective optical element and upstream from the detector and which images the radiation reflected from object points on the reflective optical element onto respective image points on the detector;
   wherein the measuring arrangement has over a predetermined wavelength interval of at least $\Delta\lambda=3$ nm a lateral spatial resolution of less than 100 µm.

20. A method for measuring optical properties of a reflective optical element with a measuring arrangement as claimed in claim 19, comprising:
   illuminating the reflective optical element with EUV radiation of the EUV light source, and imaging object points on the reflective optical element with an imaging system onto respective image points on the detector.

21. The method as claimed in claim 20, wherein the imaging of the object points on the reflective optical element onto the respective image points on the detector is performed in a plurality of substeps, which differ from one another with regard to the operating wavelength utilized in the imaging.

\* \* \* \* \*

UNITED STATES PATENT AND TRADEMARK OFFICE
CERTIFICATE OF CORRECTION

PATENT NO. : 9,709,494 B2  
APPLICATION NO. : 15/169050  
DATED : July 18, 2017  
INVENTOR(S) : Johannes Bol et al.

Page 1 of 1

It is certified that error appears in the above-identified patent and that said Letters Patent is hereby corrected as shown below:

In Column 9, Line 45, after "claim 1," please delete "the" and insert --wherein the--.

Signed and Sealed this  
Twenty-fourth Day of April, 2018

Andrei Iancu  
*Director of the United States Patent and Trademark Office*